(12) United States Patent
Tan-Malecki et al.

(10) Patent No.: US 10,278,838 B2
(45) Date of Patent: May 7, 2019

(54) EXPANDABLE STENT DELIVERY SYSTEM WITH OUTER SHEATH

(71) Applicant: Boston Scientific Scimed, Inc., Maple Grove, MN (US)

(72) Inventors: Francisca Tan-Malecki, West Lake Village, CA (US); Ronald A. Sahatjian, Lexington, MA (US); Clifford M. Liu, Randolph, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 279 days.

(21) Appl. No.: 14/263,537

(22) Filed: Apr. 28, 2014

(65) Prior Publication Data

US 2014/0257458 A1   Sep. 11, 2014

Related U.S. Application Data

(63) Continuation of application No. 12/352,832, filed on Jan. 13, 2009, now Pat. No. 8,715,332.
(Continued)

(51) Int. Cl.
*A61F 2/958* (2013.01)
*A61F 2/82* (2013.01)
(Continued)

(52) U.S. Cl.
CPC .................. *A61F 2/82* (2013.01); *A61F 2/95* (2013.01); *A61F 2/958* (2013.01); *A61F 2/966* (2013.01);
(Continued)

(58) Field of Classification Search
CPC .. A61F 2/958; A61F 2/966; A61F 2/82; A61F 2002/9583; A61M 25/10; A61M 2025/1081
See application file for complete search history.

(56) References Cited

U.S. PATENT DOCUMENTS

| | | | | |
|---|---|---|---|---|
| 4,950,227 A | * | 8/1990 | Savin | A61F 2/90 604/8 |
| 5,191,883 A | * | 3/1993 | Lennox | A61B 18/08 606/27 |

(Continued)

OTHER PUBLICATIONS

Lally, et al., "Stents", Wiley Encyclopedia of Biomedical Engineering, 2006, pp. 1-10, John Wiley & Sons, Inc.

*Primary Examiner* — Katherine M Rodjom
(74) *Attorney, Agent, or Firm* — Seager, Tufte & Wickhem, LLP (57) ABSTRACT

According to aspects described herein, there is disclosed an improved hot balloon catheter delivery system for shape memory tubular stents. An outer sheath is provided on the delivery system that facilitates stent placement on a balloon during delivery through an endoscope. In one embodiment, the stent may be positioned between radiopaque markers/electrodes and the balloon may be heated. The stent may be prevented from moving proximally relative to the catheter as the delivery system is tracked through the patient's anatomical passageways. The outer sheath may be positioned to ride over the proximal cone of the hot balloon catheter and abut the proximal end of the stent to facilitate proper alignment of the balloon for deployment. Upon deployment of the stent in an appropriate position, the sheath may be pulled away from the stent to expose the proximal cone of the balloon and thereby allow balloon and stent expansion.

20 Claims, 5 Drawing Sheets

Related U.S. Application Data (60) Provisional application No. 61/021,064, filed on Jan. 15, 2008.

(51) Int. Cl.
*A61F 2/95* (2013.01)
*A61F 2/966* (2013.01)
*A61M 25/10* (2013.01)

(52) U.S. Cl.
CPC ...... *A61F 2002/9583* (2013.01); *A61M 25/10* (2013.01); *A61M 2025/1081* (2013.01)

(56) References Cited

U.S. PATENT DOCUMENTS

| | | | |
|---|---|---|---|
| 5,334,185 A | 8/1994 | Giesy et al. | |
| 5,695,498 A | 12/1997 | Tower | |
| 5,800,516 A | 9/1998 | Fine et al. | |
| 6,395,008 B1 * | 5/2002 | Ellis | A61F 2/958 606/108 |
| 6,514,280 B1 | 2/2003 | Gilson | |
| 6,579,305 B1 * | 6/2003 | Lashinski | A61F 2/958 606/192 |
| 6,585,747 B1 * | 7/2003 | Limon | A61F 2/958 606/108 |
| 6,592,549 B2 * | 7/2003 | Gerdts | A61F 2/95 604/103.04 |
| 6,626,936 B2 | 9/2003 | Stinson | |
| 6,830,559 B2 | 12/2004 | Schock | |
| 7,127,789 B2 | 10/2006 | Stinson | |
| 2004/0181252 A1 | 9/2004 | Boyle et al. | |
| 2004/0230286 A1 * | 11/2004 | Moore | A61F 2/95 623/1.11 |
| 2004/0249435 A1 * | 12/2004 | Andreas | A61F 2/958 623/1.12 |
| 2005/0080475 A1 * | 4/2005 | Andreas | A61F 2/958 623/1.11 |
| 2006/0004439 A1 * | 1/2006 | Spenser | A61F 2/2436 623/1.23 |
| 2006/0206190 A1 * | 9/2006 | Chermoni | A61F 2/958 623/1.11 |
| 2006/0241745 A1 * | 10/2006 | Solem | A61F 2/246 623/2.18 |
| 2007/0106365 A1 | 5/2007 | Andreas et al. | |
| 2008/0172120 A1 | 7/2008 | Fenn et al. | |

* cited by examiner

EXPANDABLE STENT DELIVERY SYSTEM WITH OUTER SHEATH

PRIORITY CLAIM

This patent application is a continuation of U.S. patent application Ser. No. 12/352,832, filed Jan. 13, 2009, which claims the benefit of U.S. Provisional Patent application Ser. No. 61/021,064 filed on Jan. 15, 2008. The entire contents of each are incorporated by reference.

TECHNICAL FIELD

The present disclosed technologies generally relate to stent delivery systems and more particularly to an outer sheath addition to hot balloon catheter delivery systems for shape memory tubular stents.

BACKGROUND

A stent is generally a longitudinal tubular device formed of biocompatible material, which is useful to open and support various lumens in the body. Stents are used in various bodily passageways, such as in the coronary or peripheral vasculature, esophagus, trachea, bronchi, colon, biliary tract, urinary tract, prostate, brain, as well as in a variety of other applications in the body. These devices are implanted within the passage to open and/or reinforce collapsing or partially occluded sections. While stents and other intraluminary prosthesis are foreign objects to the human body, they are designed to remain within a body passageway for prolonged periods or even indefinitely.

Stents generally include a flexible configuration. This configuration allows the stent to be inserted through curved vessels or lumens (natural or artificial) and curved instruments, such as an endoscope. Such stents are generally delivered using a flexible elongate catheter. The catheters are designed to resist kinking and may be developed with various levels of stiffness. The stents are designed and configured to radially compress for intraluminary catheter implantation. Once properly positioned adjacent the damaged vessel or lumen, the stent is radially expanded so as to support and reinforce the vessel or lumen. Radial expansion of the stent may be accomplished by inflation of a balloon or other expanding means attached to the catheter or the stent may be of the self-expanding variety which will radially expand once deployed.

Tubular shaped structures, which have been used as intraluminary vascular stents, have included helically wound coils which may have undulations or zigzags therein, slotted stents, ring stents, braided stents and open mesh wire/filament stents, to name a few. Additionally, super-elastic and shape memory materials using plastic and/or metals have also been used to form stents.

Diagnosis and treatment in patients of biliary strictures caused by malignant or benign biliary disease is treatable. A patient with biliary disease typically suffers from an obstruction in the pancreaticobiliary ductal system. Numerous diseases can cause the inability of bile flow, however, the presence of gallstones and/or strictures appear the most prevalent reason. For benign strictures, stenting is one possible solution. In particular, tubular stents are used in bile, pancreatic and hepatic ducts where a solid stent is needed and where in-growth can occur due to proliferating oncologous cells.

Solid stents are often mounted on a balloon catheter and delivered non-invasively, such as through an endoscope, and deployed by expanding the stent to a larger diameter. For example, U.S. Pat. No. 5,191,883 to Lennox et al. and U.S. Pat. No. 6,830,559 to Schock describe balloon catheter delivery systems. Alternatively, the stent is slipped off a catheter with no expansion. For example, see U.S. Pat. No. 5,334,185 to Giesy et al. These stents are typically designed to withstand drastic deformations as it is conveyed through the twists and turns of the tortuous anatomy of a patient's gastrointestinal system.

One drawback, however, is that as the delivery system is tracked through the endoscope, the stent may slide out of its intended position. In particular, a stent may slide proximally and may no longer be disposed between radiopaque markers on and/or the electrodes used to expand the balloon located on the delivery system. Thus, once out of position, the physician may find it difficult to accurately position the stent. Also, the stent may be difficult to properly expand if improperly positioned on the balloon.

Additionally, even when the stent remains properly positioned on the delivery system, removal of the balloon after delivery can sometimes be problematic. After the stent has been fully expanded, the balloon is generally deflated before being removed. While or after being deflated, however, the balloon may get stuck to the stent. Sticking can occur due to anatomical curvatures in the delivery location which pinch or trap the balloon, stent to balloon material tackiness, a balloon wing fold getting hung-up and/or other reasons. During removal, if the balloon is stuck to the stent it can slightly pull the stent out of place or even completely out of position.

Therefore, there is a need for improved delivery systems for stents deployed using an expansion member, such as a balloon catheter. Such a system preferably overcomes the shortcomings set forth above while being relatively easily manufactured and used.

SUMMARY

An improved hot balloon catheter delivery system for shape memory tubular stents is disclosed. An outer sheath is provided on the delivery system that facilitates stent placement on a balloon during delivery through an endoscope. In one embodiment, the stent may be positioned between radiopaque markers/electrodes and the balloon may be heated. The stent may be prevented from moving proximally relative to the catheter as the delivery system is tracked through the patient's anatomical passageways. The outer sheath may be positioned to ride over the proximal cone of the hot balloon catheter and abut the proximal end of the stent to facilitate proper alignment of the balloon for deployment. Upon deployment of the stent in an appropriate position, the sheath may be pulled away from the stent to expose the proximal cone of the balloon and thereby allow balloon and stent expansion.

One aspect of the disclosed technology includes an apparatus for delivering an expandable stent into a patient through a body lumen. The apparatus includes a flexible catheter, an expansion member, a control assembly and a sheath member. The flexible catheter is for delivering the stent. The catheter may have a stent delivery portion at a distal end thereof. The expansion member may be secured to the stent delivery portion of the catheter. The expansion member may be adjustable between a collapsed state and an expanded state. The expandable stent is mounted on and circumferentially surrounds at least a portion of the expansion member, whereby adjustment of the expansion member from the collapsed state to the expanded state causes radial expansion of the stent relative to a longitudinal axis of the stent. The control assembly may actuate the expansion member between the collapsed and the expanded states. The sheath circumferentially surrounds a portion of the catheter for limiting movement of the stent relative to the catheter during delivery.

Another aspect of the disclosed technology includes an assembly for delivering a stent into a patient through a body lumen. The assembly includes an expandable stent, a flexible catheter, an expansion member, a control assembly and a sheath. The flexible catheter is for delivering the stent. The expansion member may be secured to a distal end of the catheter. The expansion member may be adjustable between a collapsed state and an expanded state. Also, the stent may be mounted on at least a portion of the expansion member, whereby adjustment of the expansion member from the collapsed state to the expanded state causes radial expansion of the stent relative to a longitudinal axis of the stent. The control assembly may actuate the expansion member between the collapsed and the expanded states. Also, the sheath circumferentially surrounds a portion of the catheter for limiting movement of the stent relative to the catheter.

Additionally, the expansion member may comprise a balloon. The balloon can include two opposed ends that when inflated during delivery are wider than a central portion of the balloon. Further, the sheath can be moveable along a length of the catheter. The sheath can be securable relative to the catheter for limiting the stent movement. Also, a distal end of the sheath can abut a proximal end of the stent. Further a distal end of the sheath can be radially wider than a central portion of the sheath. A distal end of the sheath can flare radially outwardly and/or include one or more slits passing through a wall of the sheath.

Yet another aspect of the disclosed technology includes a method for delivering an expandable stent into a patient through a body lumen. The method comprises providing a flexible balloon catheter for delivering the stent. The catheter includes an expandable balloon, a control assembly and an outer sheath. The balloon may be secured to a distal end of the catheter and may be adjustable between a collapsed state and an expanded state. The control assembly may adjust the expansion member between states. Additionally, the method comprises mounting a stent on the balloon in the collapsed state. A distal end of the sheath may abut a proximal end of the stent for limiting movement of the stent relative to the catheter. Additionally, the method comprises inserting the flexible catheter and stent into a patient through a body lumen, while maintaining a fixed relative position between the stent and the catheter. Then, the control assembly is activated to expand the stent. Thereafter, the balloon catheter may be withdrawn once the stent has expanded. The method can further include the step of advancing the sheath distally inside the stent prior to withdrawing the catheter.

These and other embodiments, features, and advantages of the disclosed technologies will become apparent from the following detailed description of illustrative embodiments thereof, which is to be read in connection with the accompanying drawings.

DETAILED DESCRIPTION OF THE PREFERRED EMBODIMENTS

The invention relates to an apparatus, system and method for insertion and/or delivery of a stent in a bodily passageway. The invention allows the clinician or operator to more accurately deliver the stent by minimizing drift or a shift of position of the stent while passing through body lumens prior to delivery. The assembly is suited for medical applications (for example, endoscopic therapy) including in the biliary tract, the gastrointestinal tract, the urinary tract, and the respiratory tract. In particular, one embodiment of the invention is directed to an assembly, system and method for delivering an intraluminary prosthesis, such as a stent in a biliary duct. Additionally, an assembly in accordance with the disclosed technology could be used in the vascular system, urogenital tract, neurological system (e.g., in the brain) and in the cardiovascular system (e.g., in the heart) and artificially created lumens. Reference herein to bodily passageways or lumens may be to vessels or passageways in any of the aforementioned tracts and systems or elsewhere in the body. While discussed below primarily in connection with delivering shape memory stents, the apparatus and systems of the disclosed technology can also be used to deliver other types of stents and prostheses (e.g., stent-grafts). Further, it should be understood that stents, as referred to herein, are not limited to tube like structures.

It should be noted that references herein to the term "distal" are to a direction away from an operator of the subject invention, while references to the term "proximal" are to a direction towards the operator of the subject invention. Accordingly, when the terms "distal" and "proximal" are used herein in the context of an assembly device that is being deployed within a body, such as a human body, by an operator, the term "distal" refers to a location within the body that is further within the body than a location that is "proximal" to the operator.

Figure 1:
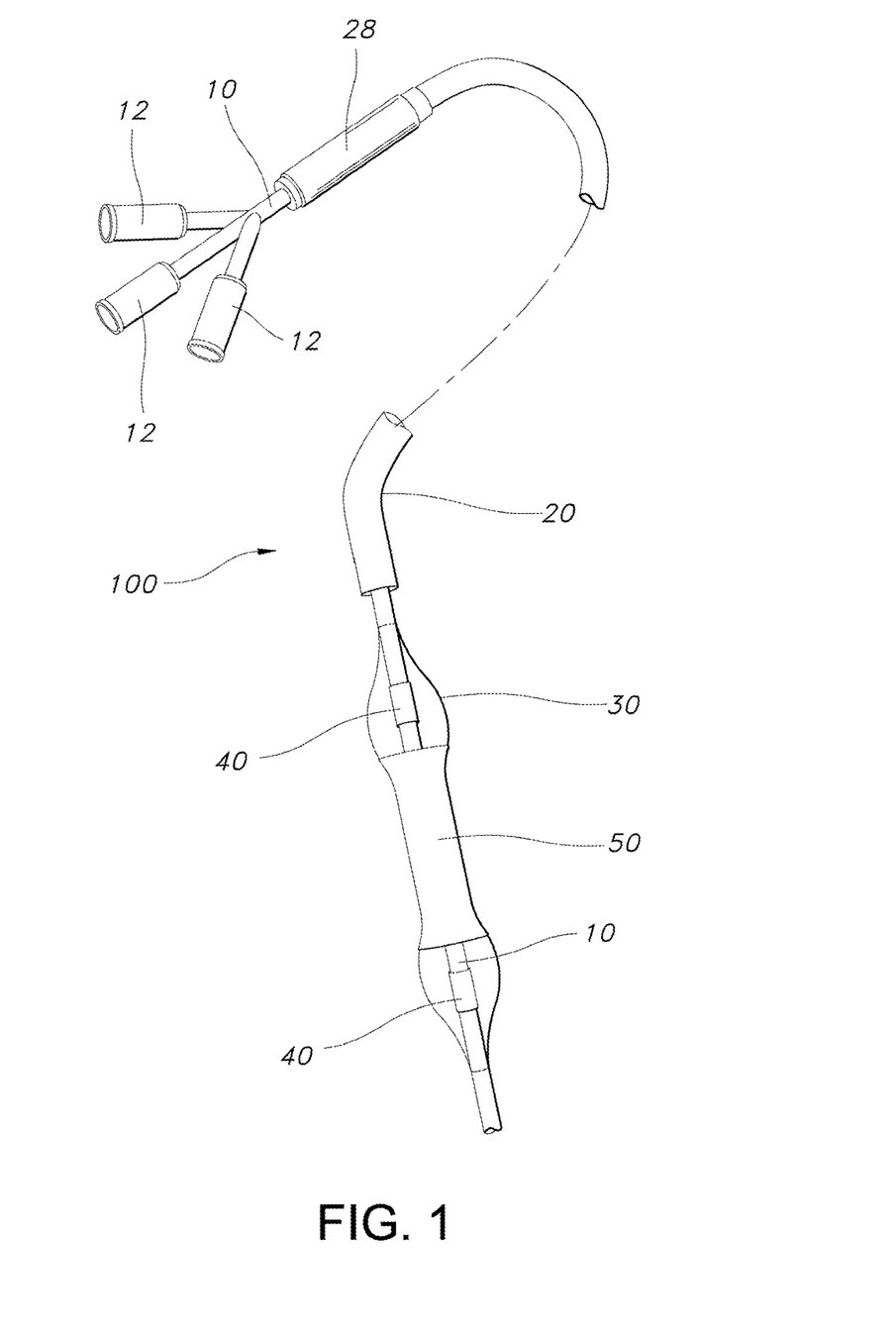
FIG. 1 is a perspective view of one aspect of a stent delivery system according to the disclosed technology.

With reference to the drawings, FIG. 1 illustrates an apparatus 100, which is a catheter delivery system used in some embodiments for shape memory tubular stents. Alternatively, the apparatus 100 can be used with non-shape memory stents that soften with the application of heat or whose shape is manipulated in other ways. Apparatus 100 includes a flexible catheter 10, a sheath member 20, an expansion member 30 and control elements 40 for activating and deactivating the expansion member 30. The middle section of the catheter 10 is removed from the illustration in order to show more detail of the proximal and distal ends of the apparatus 100. At the distal end, mounted on the expansion member 30 is an expandable stent 50 intended for insertion within a patient.

The elongate catheter 10 may be a flexible tube that is inserted into a body lumen or duct and is capable of reaching a target stent delivery location. Also, the catheter 10 may include at least one inner passage allowing drainage/injection of fluids and/or access by surgical instruments or wiring. The proximal end of the catheter 10 may be provided with openings 12 communicating with one or more passages running through the catheter 10. In this way, an inner passage can be dedicated to fluid flow, while other passages can be dedicated to wires or other control elements for the expansion member 30 at the distal end.

The sheath member 20 may surround and extend along a substantial portion of the catheter 10. At its proximal end the sheath member 20 may include a handle 28 which may allow an operator to manipulate and control the sliding movement of the sheath 20 relative to the catheter 10. The handle 28 and inner catheter 10 may include locking features (not illustrated) for at least temporarily securing those two elements relative to one another. Sheath 20 may be designed for entry into the body, and transluminal travel to a selected site in a body passageway. To this end, the sheath can be pliable in the sense that it readily bends to accommodate curved or serpentine luminal passages, yet has sufficient axial stiffness to allow control of the transluminal travel from the proximal end of the sheath. An inner sheath lumen can run longitudinally through the length of the sheath 20.

Also, sheath 20 can be preferably formed of a body compatible material. Desirably, the biocompatible material is a biocompatible polymer. Examples of suitable biocompatible polymers include, but are not limited to, polypropylene (PP), polytetrafluoroethylene (PTFE), polyethylene terephthalate (PET), high density polyethylene (HDPE) and the like. Additionally, the sheath 20 could have layers, coverings, films, coatings, and the like, desirably a polymeric covering, disposed over the outer or inner surfaces to improve interaction with the body lumen and the inner elements discussed below. Further, the sheath 20 or select portions thereof could be clear, opaque, translucent, colored and/or non-transparent as desired.

Additionally, it should be understood that the materials of the sheath 20 as well as any component filaments of the sheath 20 can be further enhanced with coverings, films, coatings, surface modifications and/or structures and other materials and techniques. A covering may be composed of polymeric material and/or silicone. The covering may also comprise any plastic or polymeric material, including a somewhat hard but flexible plastic or polymeric material. The covering may be transparent or translucent, desirably substantially or partially transparent. Furthermore, the covering may be constructed of any suitable biocompatible materials, such as, but not limited to, polymers and polymeric materials, including fillers such as metals, carbon fibers, glass fibers or ceramics. Useful covering materials include, but are not limited, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. The coating or coatings may be on the entire sheath 20 or portions thereof.

The expansion member 30 can be preferably a balloon element that can be inflated and deflated in a controlled manner in order to deploy the stent 50. Examples of balloons used as expansion members 30 are described in U.S. Pat. No. 5,191,883 to Lennox et al. (Lennox) and U.S. Pat. No. 6,830,559 to Schock. The activation of the expansion member 30 from a contracted state to an inflated/expanded state and vise-versa may be regulated by control elements 40. Only a distal portion of the overall control elements 40 are illustrated in the drawings. In particular, the two elements 40 illustrated in FIGS. 1-2 represent electrodes for activating the expansion member 30. At least one electrode is needed for this manner of delivery. Such electrodes are preferably part of a contemporary hot-balloon catheter control system as described in Lennox. However, it should be understood that other balloon catheter techniques or even other mechanical equivalents can be used as an expansion member with control elements in accordance with the disclosed technology.

Additionally, the elements 40 also may include radiopaque markers. The radiopaque markers can either be incorporated with the electrodes described above or disposed in proximity thereto. Preferably, a pair of electrodes and a pair of markers are included in the distal end of the catheter 10. The electrodes can also be radiopaque, thus eliminating the need for separate markers. The markers 40 can assist the physician or operator in visualizing the relative position of the delivery portion of the apparatus 100 with relation to the target delivery location. Such markers 40 can be formed from radiopaque materials, such as metallic-based powders or ceramic-based powders, particulates or pastes which may be incorporated into the distal catheter material. For example, the radiopaque material may be blended with the polymer composition from which the polymeric filament is formed, and subsequently fashioned into a portion of the catheter 10. Alternatively, the radiopaque material may be applied only to the surface of the catheter 10. As a further alternative, the radiopaque material may be attached to the stent (for example, attached or clipped-on mechanically or chemically through adhesives, etc.). Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated by reference. Metallic complexes useful as radiopaque materials are also contemplated. The markers 40 may be the only portion made radiopaque or the entire distal portion of the catheter 10 can be made radiopaque. Further, the distal portion of the catheter 10 may have an inner core of tantalum, gold, platinum, iridium or combinations thereof and an outer member or layer of nitinol to provide a composite filament for improved radiocapicity or visibility. Alternatively, portions of the catheter 10 may designed for improved external imaging under magnetic resonance imaging (MRI) and/or ultrasonic visualization techniques. MRI is produced by complex interactions of magnetic and radio frequency fields. Materials for enhancing MRI visibility include, but are not limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the area represented by markers 40 of the disclosed technology may include ultrasound resonant material, such as but not limited to gold.

Also illustrated in FIG. 1 is the stent 50. The stent 50 can be formed of plastics, metals or other materials, it is preferred that a biocompatible construction is employed. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks and polytetrafluoroethylenes. The polymeric materials may further include a metallic, a glass, ceramic or carbon constituent or fiber. Useful and nonlimiting examples of bioabsorbable or biodegradable polymeric materials include poly (L-lactide) (PLLA), poly(D,L-lactide) (PLA), poly (glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Useful biocompatible materials include but are not limited to biocompatible metals, biocompatible alloys, biocompatible polymeric materials, including synthetic biocompatible polymeric materials and bioabsorbable or biodegradable polymeric materials, materials made from or derived from natural sources and combinations thereof. Useful biocompatible metals or alloys include, but not limited to, nitinol, stainless steel, cobalt-based alloy such as Elgiloy, platinum, gold, titanium, tantalum, niobium, polymeric materials and combinations thereof. These alloys may also be doped with small amounts of other elements for various property modifications as may be desired and as is known in the art. Further, the stent 50 may include materials made from or derived from natural sources, such as, but not limited to collagen, elastin, glycosaminoglycan, fibronectin and laminin, keratin, alginate, combinations thereof and the like. Alternatively, a portion of the stent 50 may comprise a resilient spring-like metal for selfexpansion, while a second portion is a deformable metal for final sizing. It should be understood that shape memory elements may be discrete or merely different phases of an alloy.

Figure 2A:
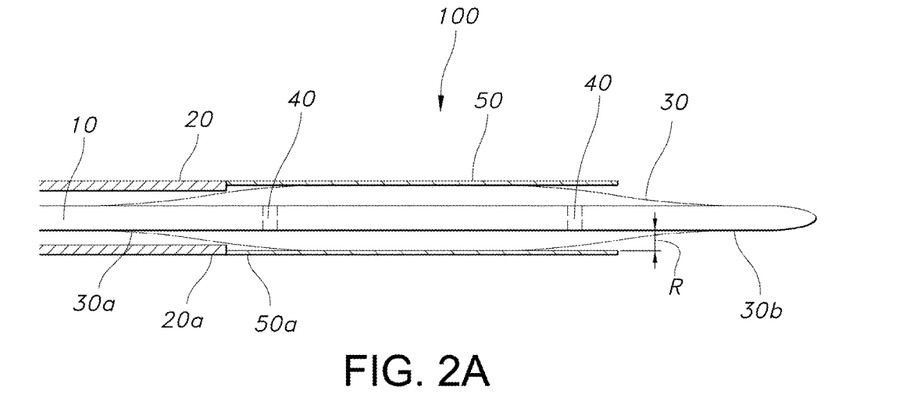
FIGS. 2A-D are sectional views of one embodiment the distal end of the stent delivery system during progressive phases of releasing and delivering a stent according to the disclosed technology.
Figure 2B:
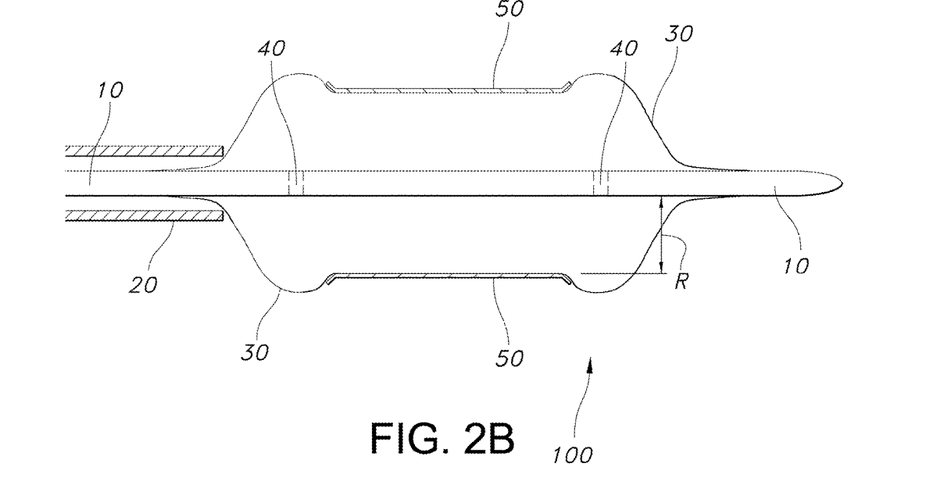

Referring to FIG. 2A-2B, apparatus 100 is illustrated in various stages of deployment of stent 50. FIG. 2A illustrates the distal end of the apparatus 100 with the stent 50 mounted thereon for delivery. Preferably, the configuration illustrated may be maintained while the physician inserts and tracks the apparatus 100 to the desired location within the patient. The expansion member 30, in the form of an expandable balloon may be secured at two ends 30a and 30b to the catheter 10. The expansion member 30 is illustrated in a deflated/collapsed state. The expansion member 30 may be positioned to cover and contain the electrodes 40, which are part of the control assembly for actuating the expansion of the balloon 30. The location of each electrode 40 may include radiopaque markers. In this way, the area between the two markers 40 represents the delivery portion of the catheter. Thus, by mounting the stent 50 over the delivery portion, the physician can use the markers 40 to track and accurately position the stent 50 in the patient.

Also illustrated in FIG. 2A is sheath member 20 disposed radially adjacent and axially surrounding the stent 50. Prior to insertion within the patient, distal sheath end 20a may be positioned to abut the proximal stent end 50a, as shown. Alternatively, a distal portion of the sheath 20 can be configured to hold and axially surround the stent 50, expansion member 30 and the distal end of the catheter 10. In this alternative design, the sheath 20 can then be pulled back to the position illustrated in FIG. 2A, just prior to expansion of the stent 50. Once positioned as illustrated in FIG. 2A, preferably either design allows the sheath handle 28 to be secured relative to the catheter 10 in order to limit axial movement of the stent 50 relative to the delivery portion.

FIG. 2B illustrates the expansion member 30 expanded, thereby expanding the stent 50 to a desirable radius R. It should be noted that while radius R, illustrated in FIG. 2B, is preferably larger than the smaller compressed radius r, illustrated in FIG. 2A, the actual dimensions can vary from those illustrated in the drawings. In other words, the dimensions illustrated are for exemplary purposes only, and the actual dimensions would be designed and configured to conform to the intended stent application. The control assembly 40 is carefully regulated to ensure the requisite expansion dimensions for the stent 50. During expansion, it may be desirable to use a balloon 30 that expands into a dog-bone shape, as illustrated, in order to further maintain the stent 50 generally centered between the markers 40. Alternatively, a cage, basket or other device could be used to expand the stent 50.

Figure 2C:
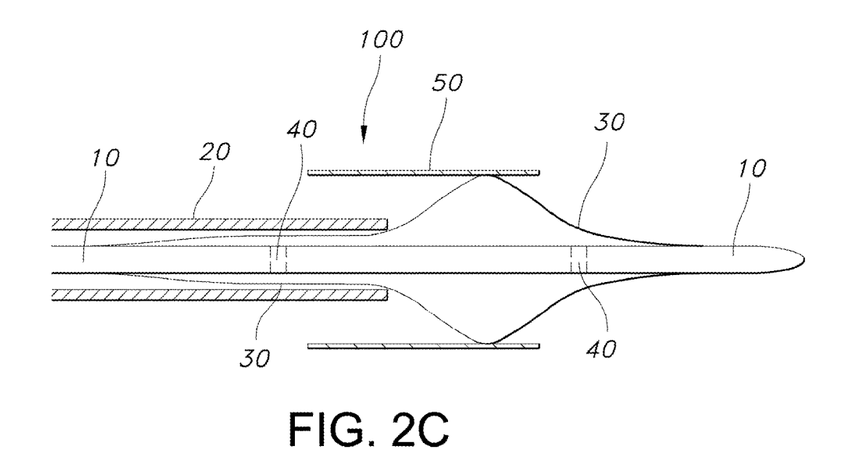
Figure 2D:
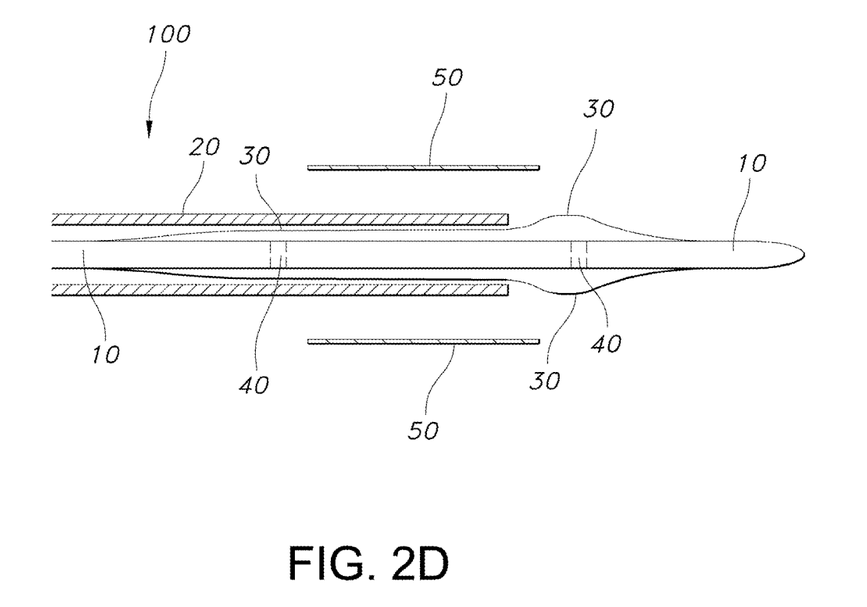

FIG. 2c illustrates the apparatus 100 after the stent 50 has been expanded and the expansion member 30 has been partially contracted or deflated. Also illustrated is an example of when expansion member 30 can get caught or stuck on the stent 50. To assist in separating the expansion member 30 from the stent 50, the sheath 20 can be advanced distally into the expanded stent 50. This may help pull the expansion member 30 away from the stent 50 without moving the stent 50 out of position. Once the sheath 20 is advanced distally beyond the stent, or when the physician is confident the expansion member 30 is not stuck to the stent 50, the entire delivery system can be pulled back, as illustrated in FIG. 2D, or completely withdrawn. In this way, the stent 50 should remain in its intended delivery location and the apparatus 100 can be safely removed. Additionally, prior to removal the sheath 20 could be used to deliver relatively hot, cold or thermally neutral fluids.

Figure 3:
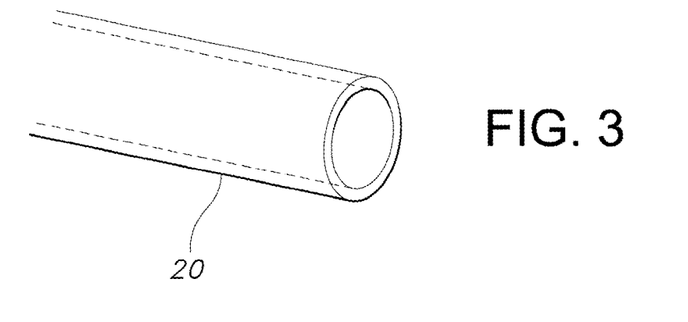
FIG. 3 is a perspective view of one embodiment the distal end of the moveable sheath according to the disclosed technology.
Figure 4:
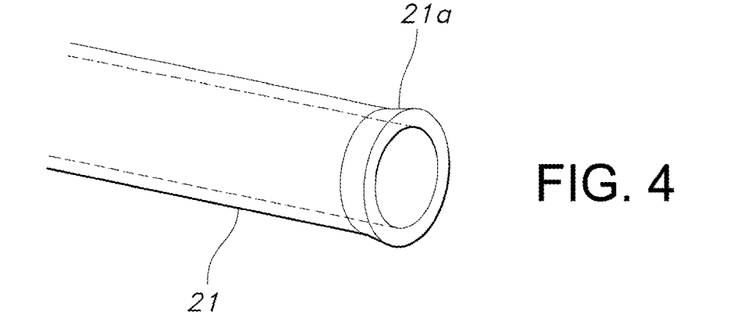
FIG. 4 is a perspective view of one embodiment the distal end of the moveable sheath according to an alternative embodiment of the disclosed technology.

FIGS. 3-7 illustrates various embodiments of the distal end of the sheath member 20. FIG. 3 illustrates a sheath member 20 with a continuous circular cross-section. FIG. 4 illustrates a sheath member 21 whose distal end 21a bulges radially outward. The bulging end 21a can further assist in separating the stent 50 from the expansion member 30 after delivery.

Figure 5:
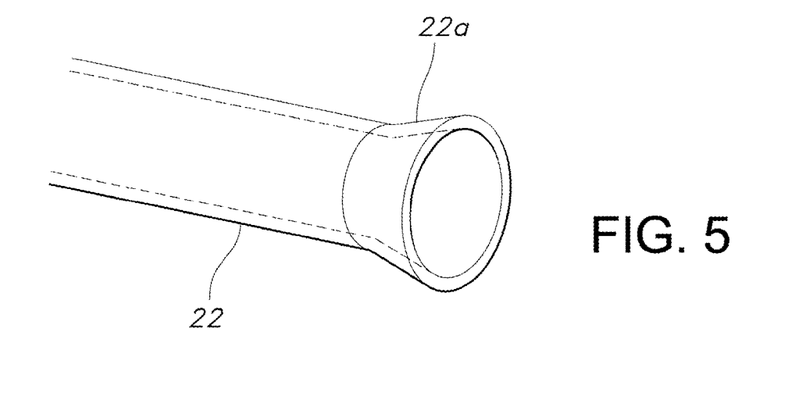
FIG. 5 is a perspective view of one embodiment the distal end of the moveable sheath according to another alternative embodiment of the disclosed technology.

FIG. 5 illustrates a sheath member 22 whose distal end 22a flares radially outwardly, like a funnel or cone. A flared distal end 22a can alternatively be used as an anchor against the proximal end of the expanded stent 50. Thus, the sheath 22 can prevent further stent movement as the expansion member 30 is pulled back inside the sheath 22. It should be understood that the pitch and length of the flared distal end 22a can vary as suited for the particular stent and delivery conditions.

Figure 6:
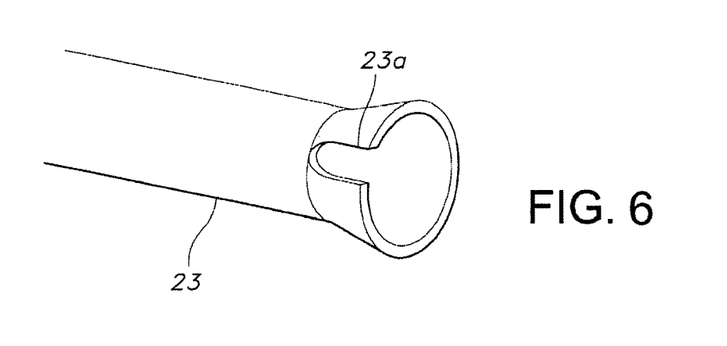
FIG. 6 is a perspective view of one embodiment the distal end of the moveable sheath according to another alternative embodiment of the disclosed technology.
Figure 7:
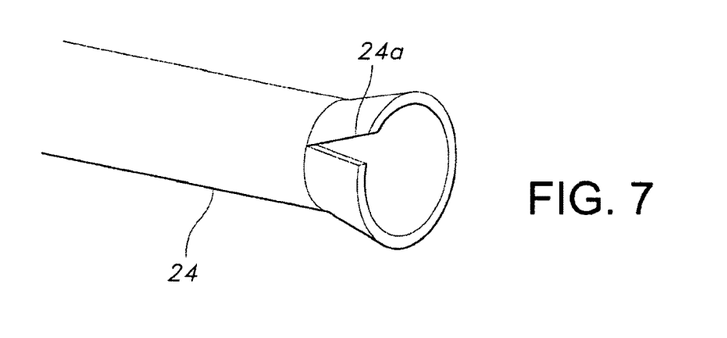
FIG. 7 is a perspective view of one embodiment the distal end of the moveable sheath according to another alternative embodiment of the disclosed technology.

FIGS. 6 and 7 illustrate further alternative sheath members 23, 24 whose distal ends include cutouts or slits 23a, 24a. The slit 23a may have a rounded end while the slit 24a may have a straight taper. However, it should be understood that slits with other shapes could also be advantageous. The slits 23a, 24a can further assist in separating the expansion member 30 from the expanded stent 50. Additionally, the slits 23a, 24a can be used to maintain a desired rotational relationship between the stent 50 and the delivery system 100. In other words, in addition to preventing the stent from sliding axially in the proximal direction relative to the catheter 10, the slit can prevent the stent from rotating relative to the catheter 10 via the expansion member 30. Distal end of sheath may be rounded to assist forward movement.

Further, it should be understood that further techniques can be used in conjunction with the apparatus, system and methods described above, to ensure and facilitate accurate stent delivery. For example, altering balloon materials, applying a lubricant between the balloon and stent and/or leaving out pre-shrinking when mounting the stent on the balloon, can reduce sticking between the stent and the balloon. Similarly, changing how the balloon is folded into its compressed state, such as reducing or reorienting the wing folds of the balloon, can further assist in this regard. The sheath may have varying stiffness, varying reinforced layers, reinforcement, varying wall thickness, varying diameters, varying cross-sectional geometry.

While various embodiments of the present invention are specifically illustrated and/or described herein, it will be appreciated that modifications and variations of the present invention may be effected by those skilled in the art without departing from the spirit and intended scope of the invention.

What is claimed is:

1. A stent delivery catheter having an outer surface, the stent delivery catheter comprising:
   a tube having a proximal end, a distal end, and a length measured from the proximal end to the distal end;
   a sheath extending along a majority of the length of the tube, the sheath defined by a continuous circumferential wall at a distal end thereof;
   the tube extending through a lumen of the sheath and longitudinally moveable relative thereto;
   an expansion member secured to the tube;
   a stent positioned around and in direct contact with the expansion member in an unexpanded configuration; and
   a control assembly for actuating expansion of the expansion member; wherein:
   the distal end of the sheath abuts a proximal end of the stent forming a continuous surface, the continuous surface forming a part of the outer surface of the stent delivery catheter, wherein the continuous surface is at a radially outermost extent of the stent delivery catheter during advancement of the stent delivery catheter through a body lumen, wherein an inner diameter of the distal end of the sheath is less than an outer diameter of the stent in the unexpanded configuration.

2. The stent delivery catheter of claim 1, wherein the expansion member is a balloon.

3. The stent delivery catheter of claim 2, wherein the sheath overlays a proximal end and a proximal cone of the balloon.

4. The stent delivery catheter of claim 1, wherein the sheath includes a handle.

5. The stent delivery catheter of claim 1, wherein the proximal end of the tube includes an opening in communication with a longitudinal passage of the tube.

6. The stent delivery catheter of claim 1, wherein the stent delivery catheter is positioned inside a lumen of an endoscope.

7. The stent delivery system of claim 1, further comprising an electrode positioned between opposite ends of the expansion member.

8. The stent delivery system of claim 1, wherein an outer diameter of the distal end of the sheath is the same as the outer diameter of the stent in the unexpanded configuration.

9. A stent delivery system having an outer surface, the stent delivery system comprising:
   an endoscope defining a lumen; and
   a stent delivery catheter positioned in the lumen of the endoscope; the stent delivery catheter having a delivery configuration, and a deployment configuration for expansion of a stent, the stent delivery catheter being in the deployment configuration after the delivery configuration; the stent delivery catheter comprising: a sheath defined by a continuous circumferential wall at a distal end thereof; a stent; a balloon having two ends; a tube; and a control assembly for actuating expansion of the balloon; the stent delivery catheter being in the delivery configuration wherein:
   a proximal end region of the stent delivery catheter comprises a handle of the sheath and a proximal end of the tube, the tube having a greater longitudinal length than the sheath, the sheath extending along a majority of the longitudinal length of the tube;
   the tube positioned in a lumen of the sheath and longitudinally moveable relative thereto;
   the balloon secured to the tube;
   the stent positioned around and in direct contact with the balloon; and
   the distal end of the sheath abuts a proximal end of the stent to form a continuous surface, the continuous surface forming a part of the outer surface of the stent delivery catheter in the delivery configuration, wherein the continuous surface is at a radially outermost extent of the stent delivery catheter during advancement of the stent delivery catheter through a body lumen, wherein an inner diameter of the distal end of the sheath is less than an outer diameter of the stent in the delivery configuration and the sheath overlays a proximal cone of the balloon in the delivery configuration.

10. The stent delivery system of claim 9, wherein when the stent delivery catheter is in the deployment configuration the sheath is proximal to the proximal cone of the balloon and a proximal end of the stent for expansion of the balloon and deployment of the stent.

11. The stent delivery system of claim 10, further wherein in the deployment configuration, the balloon is expandable for deployment of the stent.

12. The stent delivery system of claim 9, wherein a proximal end of the tube includes an opening in communication with a longitudinal passage of the tube.

13. The stent delivery system of claim 9, the sheath having a continuous circular cross-section.

14. The stent delivery system of claim 9, further comprising an electrode positioned between the two ends of the balloon, wherein the electrode is configured to heat the balloon.

15. The stent delivery system of claim 9, wherein an outer diameter of the distal end of the sheath is the same as the outer diameter of the stent in the delivery configuration.

16. A stent delivery catheter comprising:
   a tube having a proximal end, a distal end, and a length measured from the proximal end to the distal end;
   a sheath extending along a majority of the length of the tube, the sheath defined by a continuous circumferential wall at a distal end thereof, the circumferential wall defining a portion of an outer surface of the stent delivery catheter;

the tube extending through a lumen of the sheath and longitudinally moveable relative thereto;

a balloon secured to the tube; and a stent having a proximal end and a distal end, the stent being radially expandable from an unexpanded state in a delivery configuration of the stent delivery catheter to an expanded state in a deployment configuration of the stent delivery catheter, the stent positioned around and in direct contact with the balloon in the unexpanded state such that the distal end of the sheath abuts the proximal end of the stent forming a continuous surface, the continuous surface forming a part of the outer surface of the stent delivery catheter, wherein the continuous surface is at a radially outermost extent of the stent delivery catheter during advancement of the stent delivery catheter through a body lumen;

wherein an inner diameter of the distal end of the sheath is less than an outer diameter of the stent in the unexpanded state;

wherein in the delivery configuration, the balloon is in a deflated state; and wherein in the deployment configuration the balloon is in an inflated state to radially expand the stent to the expanded state.

17. The stent delivery catheter of claim 16, wherein when the stent delivery catheter is in the deployment configuration the distal end of the sheath is proximal to a proximal cone of the balloon and proximal to the proximal end of the stent for expansion of the balloon and deployment of the stent.

18. The stent delivery catheter of claim 17, wherein the sheath overlays the proximal cone of the balloon in the delivery configuration.

19. The stent delivery catheter of claim 16, wherein the proximal and distal ends of the stent are positioned between proximal and distal ends of the balloon in both the delivery configuration and the deployment configuration.

20. The stent delivery catheter of claim 19, wherein in the inflated state, the proximal end and the distal end of the balloon are wider than a central portion of the balloon.

* * * * *